United States Patent
Fujikake (10) Patent No.: US 10,507,156 B2
(45) Date of Patent: Dec. 17, 2019

(54) LOAD DETECTING DEVICE AND WALK ASSISTING DEVICE

(71) Applicant: TOYOTA JIDOSHA KABUSHIKI KAISHA, Toyota-shi, Aichi-ken (JP)

(72) Inventor: Yoshinori Fujikake, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 917 days.

(21) Appl. No.: 14/930,236

(22) Filed: Nov. 2, 2015

(65) Prior Publication Data
US 2016/0151228 A1   Jun. 2, 2016

(30) Foreign Application Priority Data

Nov. 27, 2014   (JP) .................................. 2014-239997

(51) Int. Cl.
| | | |
|---|---|---|
| *A61H 3/00* | (2006.01) | |
| *A61B 5/103* | (2006.01) | |
| *A61B 5/00* | (2006.01) | |
| *A61F 2/70* | (2006.01) | |
| *A61F 2/60* | (2006.01) | |

(52) U.S. Cl.
CPC ............. *A61H 3/00* (2013.01); *A61B 5/1038* (2013.01); *A61B 5/6807* (2013.01); *A61F 2/70* (2013.01); *A61F 2002/607* (2013.01); *A61F 2002/701* (2013.01); *A61F 2002/704* (2013.01); *A61F 2002/705* (2013.01); *A61H 2003/005* (2013.01); *A61H 2003/007* (2013.01)

(58) Field of Classification Search
CPC .... A61H 3/00; A61H 1/024; A61H 2201/164; A61H 2201/5061; A61H 2201/5097; A61H 2201/1215; A61H 2201/165; A61H 2003/007; A61H 2003/005; A61F 2/70; A61F 2002/704; A61F 2002/607; A61F 2002/705; A61F 2002/701; A61B 2562/0247

See application file for complete search history.

(56) References Cited

U.S. PATENT DOCUMENTS

| | | | | |
|---|---|---|---|---|
| 4,647,918 A * | 3/1987 | Goforth | ............... | A43B 3/0005 340/573.1 |
| 4,814,661 A * | 3/1989 | Ratzlaff | .................. | A01L 11/00 310/319 |
| 7,998,092 B2 * | 8/2011 | Avni | .................... | A61B 5/1036 600/587 |
| 9,192,816 B2 * | 11/2015 | Molyneux | ............ | A43B 3/0005 |
| 9,279,734 B2 * | 3/2016 | Walker | .................. | G01L 1/2206 |

(Continued)

FOREIGN PATENT DOCUMENTS

| | | |
|---|---|---|
| CN | 101917902 A | 12/2010 |
| JP | S63-154029 U | 10/1988 |

(Continued)

*Primary Examiner* — Steven O Douglas
(74) *Attorney, Agent, or Firm* — Oliff PLC (57) ABSTRACT

A load detecting device includes a sole shape portion that is formed along a shape of a sole of a walk trainee, and on which the sole gets, a flare portion that is formed so as to project outside the sole shape portion, a first load sensor that is provided at the sole shape portion and detects the load of the sole shape portion, and a second load sensor that is provided at the flare portion and detects the load of the flare portion.

7 Claims, 6 Drawing Sheets

(56) References Cited

U.S. PATENT DOCUMENTS

| | | | |
|---|---|---|---|
| 9,549,585 B2 * | 1/2017 | Amos | G01C 22/006 |
| 10,070,680 B2 * | 9/2018 | Molyneux | A43B 3/00 |
| 2004/0169504 A1 | 9/2004 | Son et al. | |
| 2010/0271051 A1 | 10/2010 | Sankai et al. | |
| 2012/0172770 A1 | 7/2012 | Almesfer et al. | |

FOREIGN PATENT DOCUMENTS

| | | |
|---|---|---|
| JP | 2004-255563 A | 9/2004 |
| JP | 2012-011136 A | 1/2012 |
| JP | 2012532001 A | 12/2012 |
| JP | 2013-072729 A | 4/2013 |
| JP | 2013-090860 A | 5/2013 |
| JP | 2013-092507 A | 5/2013 |
| WO | 2009/084387 A1 | 7/2009 |
| WO | 2011002306 A1 | 1/2011 |

* cited by examiner

LOAD DETECTING DEVICE AND WALK ASSISTING DEVICE

INCORPORATION BY REFERENCE

This application is based upon and claims the benefit of priority from Japanese patent application No. 2014-239997, filed on Nov. 27, 2014, the disclosure of which is incorporated herein in its entirety by reference.

BACKGROUND OF THE INVENTION

1. Field of the Invention

The invention relates to a load detecting device and a walk assisting device that detects a load loaded on the sole of a walking trainee.

2. Description of Related Art

A load detecting device in which load sensors for measuring a load of a sole are disposed along approximate outline shape of a sole is known (for example, refer to International Patent Publication No. WO2009/084387).

Incidentally, for example, in a walk training device which is equipped with a walking trainee such as a hemiplegia patient who is easy to be unbalanced, a flare portion projecting can be provided at a sole shape portion on which a sole gets, the flare portion projecting outside the sole shape portion. However, as shown in the afore-mentioned walk training device, if the load sensors are disposed only within the sole shape, the detecting area of the load can be limited within the sole shape.

SUMMARY OF THE INVENTION

The present invention has been accomplished to solve the above problem and an object of the present invention is thus to provide a load detecting device and a walk assisting device capable of improving the detecting accuracy by extending the detecting area of a sole of a walk trainee.

To achieve the above object, one aspect of the present invention is a load detecting device comprising:

a sole shape portion that is formed along a shape of a sole of a walk trainee, and on which the sole gets;

a flare portion that is formed so as to project outside the sole shape portion;

a first load sensor that is provided at the sole shape portion and detects the load of the sole shape portion; and a second load sensor that is provided at the flare portion and detects the load of the flare portion.

In this aspect, the load detecting device may further comprise center calculation means for calculating a center of the sole load of the walk trainee based on the load detected by the first and second load sensors.

In this aspect, two first load sensors may be provided on the toe side of the sole shape portion, one first load sensor may be provided on the heel side of the sole shape portion, and one first load sensor may be provided on the flare portion.

In this aspect, the load detecting device may further comprise storage means for storing calibration data of the first and second load sensors.

In this aspect, the load detecting device may further comprise communication means for transmitting load data and/or calibration data of the first and second load sensors via a wireless.

To achieve the above object, one aspect of the present invention may also be a walk assisting device comprising:

a first load detecting device according to any one of Claims 1 to 5;

a thigh frame that is coupled to a first load detecting device via a ankle joint portion;

a crus frame that is coupled to the thigh frame via a knee joint portion; and a driving unit that drives the knee joint portion.

In this aspect, the walk assisting device may further comprise a second load detecting device according to any one of Claims 1 to 5 that is equipped for a good leg of the walk trainee, and all center calculation means for calculating the center of all load in grounding with both a good leg and an affected leg, based on the load detected by the first load sensor of the first load detecting device and the second load sensor of the second load detecting device.

According to the present invention, it is possible to provide a load detecting device and a walk assisting device capable of improving the detecting accuracy by extending the detecting area of a sole of a walk trainee.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

Embodiments of the present invention are described hereinafter with reference to the drawings.

Figure 1:
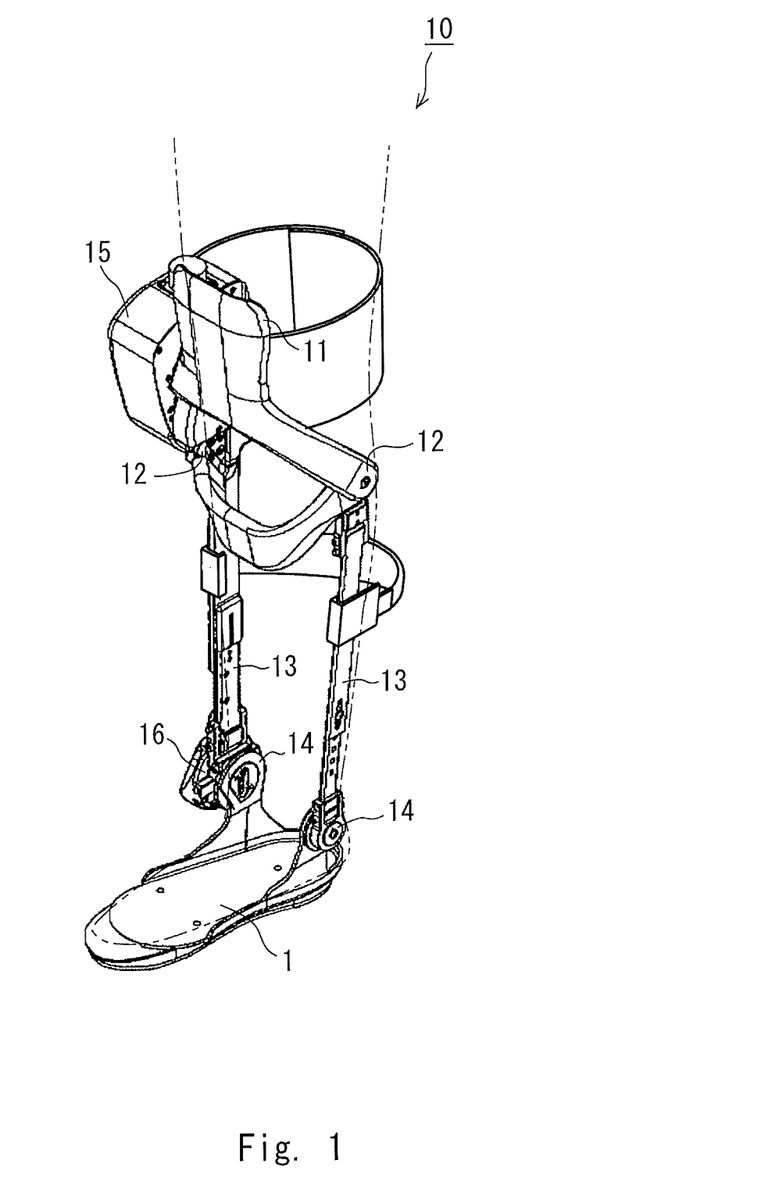
FIG. 1 is a squint view showing a schematic constitution of a walk assisting device according to an embodiment of the invention.

FIG. 1 is a squint view showing a schematic constitution of a walk assisting device according to an embodiment of the invention. The walk assisting device 10 according to the embodiment, for example is equipped with an affected (diseased) leg of a user for which a walk training is performed and assists the walking of the user. The walk assisting device 10 includes a thigh frame 11, a crus frame 13 coupled to the thigh frame 11 via a knee joint portion 12, a load detecting device 1 coupled to the crus frame 13 via an ankle joint portion 14, a driving unit 15 driving the knee joint portion 12, and an adjusting mechanism 16 adjusting a movable range of the ankle joint portion 14.

The driving unit 15 assists the walking of a user by rotatably driving the knee joint portion 12 according to the walking action of the user. The driving unit 15 includes a motor rotatably driving the knee joint portion 12 and a controller controlling the motor. Note that the afore-mentioned constitution of the walk assisting device is an example, it is not limited to this. An optional walk assisting device which can be equipped with a leg portion of a user and assist the walking is applicable. For example, the walk assisting device 10 may include a motor rotatably driving the ankle joint portion 14.

Figure 2:
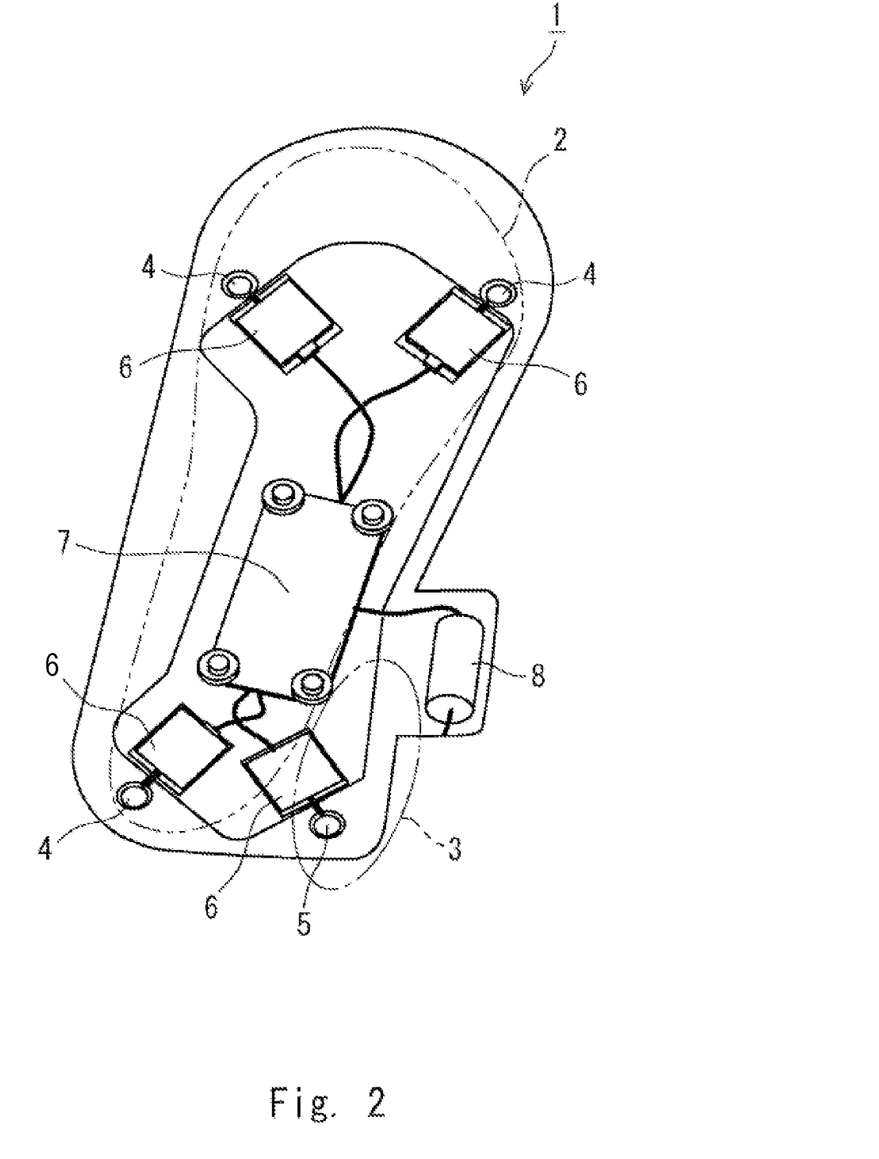
FIG. 2 is a top and squint view showing a schematic constitution of a load detecting device according to an embodiment of the invention.
Figure 3:
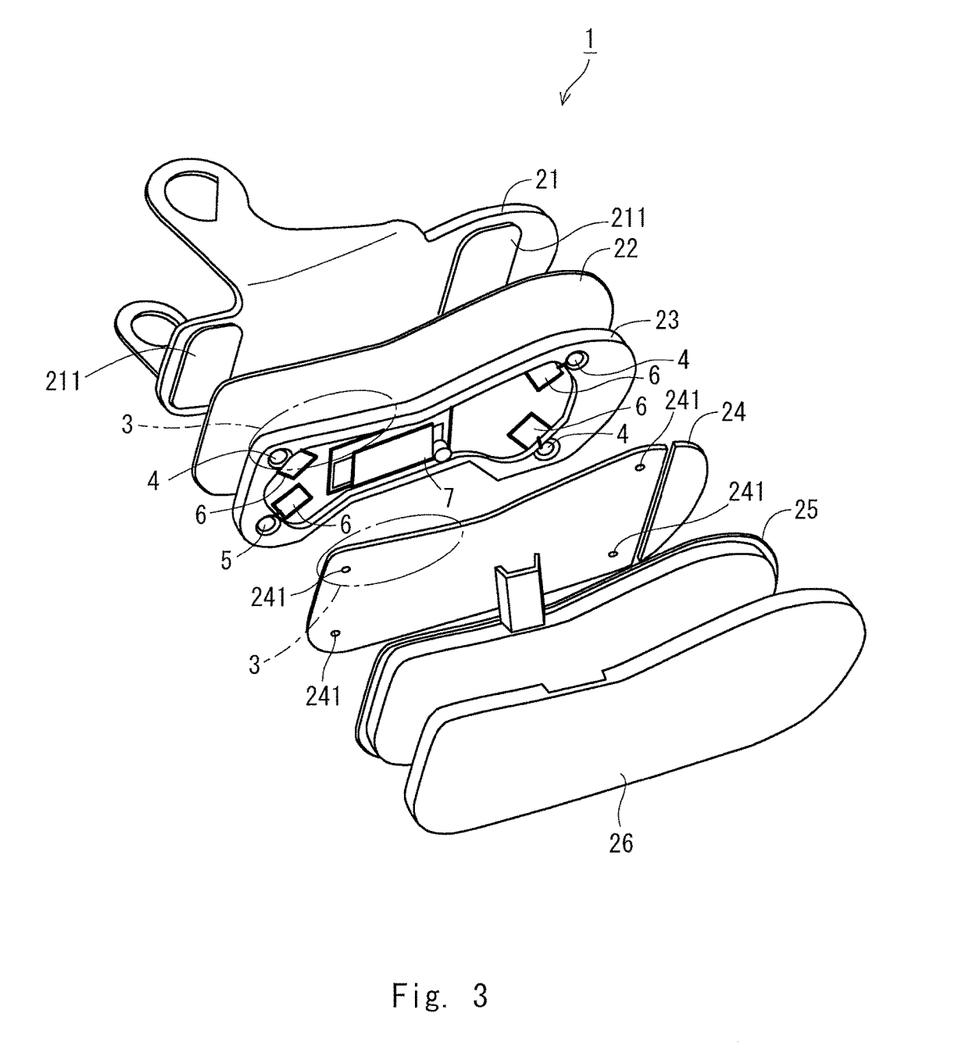
FIG. 3 is a disassembly and squint view showing a schematic constitution of a load detecting device according to an embodiment of the invention.

FIG. 2 is a top and squint view showing a schematic constitution of a load detecting device according to an embodiment of the invention. FIG. 3 is a disassembly and squint view showing a schematic constitution of a load detecting device according to an embodiment of the invention. The load detecting device 1 according to the embodiment, as shown in FIG. 2, includes a sole shape portion 2 on which a sole gets, a flare portion 3 formed outside the sole shape portion 2, a plurality of first load sensors 4 provided at the sole shape portion 2, and at least one second load sensor 5 provided at the flare portion 3.

The sole shape portion 2 is formed along the sole shape of a walk trainee and is a portion on which a sole gets. The flare portion 3 projects outside the sole shape portion 2 and is a portion formed on the heel side. The flare portion 3 has a function for preventing from falling down that for example in case a sole load of a hemiplegia patient who is easy to be unbalanced leans to the heel side, the flare portion contacts a road surface and supports the load to prevent from falling down. The flare portion 3 for example projects outside the sole shape portion 2 by approximately 20 mm and is formed on the heel side.

Note that the sole shape portion 2 and the flare portion 3 are integrated and formed, however may be separately formed. Integrating and forming the sole shape portion 2 and the flare portion enables the reduction of the manufacturing cost. Two first load sensors 4 are provided on the toe side of the sole shape portion 2, one first load sensor 4 is provided on the heel side respectively, and first load sensors 4 detect the load of the sole shape portion 2. For example, one second load sensor 5 is provided at the flare portion 3 and detects the load of the flare portion 3. The respective first and second load sensor 4, 5 are constituted of e.g. a piezoelectric element and the like. The respective first and second load sensor 4, 5 are sensors of same sort, however it is not limited to this. They may be sensors of different sort.

Incidentally, as afore-mentioned, for a walk trainee who is easy to be unbalanced, the flare portion is provided outside the sole shape portion. Then, if the load sensors are disposed only within the sole shape, the problem occurs that the detecting area of the load can be limited within the sole shape.

In regard to this, in the load detecting device 1 according to the embodiment, as afore-mentioned, the second load sensor 5 is provided at the flare portion 3. Therefore, the detecting area of the load can be extended not only within the sole shape but also to the flare portion 3. That is, the detecting accuracy can be improved by extending the detecting area of a sole of a walk trainee.

Note that, as afore-mentioned, it is possible to easily determine whether the COP (Center of Pressure) gets out of the sole shape or not, for example in a heel-contacting of a walk trainee by extending the detecting area of the load to the flare portion 3. Accordingly, the gait state of the walk trainee can be easily grasped.

Further, the detecting area of the load is extended without increasing the number of the load sensor, and the load detecting device can be constituted of four load sensors in which the number of the load sensors is minimum in calculating the center of pressure. Accordingly, the number of the load sensors can be restrained within a minimum requirement to reduce the cost. Furthermore, in the conventional load detecting device, for example, two load sensors are provided with the plantar arch portion and it is constituted of totally six load sensors in order to extend the detecting area of the load. Meanwhile, the load detecting device 1 according to the embodiment is constituted of four load sensors. Therefore, it becomes unnecessary for the load sensor to be provided with the plantar arch portion, thereby a later-mentioned micro substrate and the like can be disposed on the space and an efficient application of the space can be realized.

The load detecting device 1 according to the embodiment, as shown in FIG. 3, a stirrup portion 21, a nylon member 22 provided with the undersurface of the stirrup portion 21, a sensor holder 23 provided with the undersurface of the nylon member 22, a base plate 24 provided in down side of the sensor holder 23, a pouch member 25 provided with the undersurface of the base plate 24, and a size adjusting sole 26 provided with the undersurface of the pouch member 25.

The stirrup portion 21 is coupled to the crus frame 13 via the ankle joint portion 14, and is a high rigid member which is contact with the sole of a walk trainee. A projection portion 211 projecting in a downward direction is provided with the undersurface of the toe and heel side of the stirrup portion 21 respectively. The respective projection portion 211 is formed corresponding to the position where the first and second load sensors 4, 5 are provided. Accordingly, when the sole of a walk trainee gets on the stirrup portion 21, the respective projection portion 21 securely pushes the first and second load sensors 4, 5, thereby the sensor sensitivity is improved.

The edge shape of the stirrup portion 21, the nylon member 22, the sensor holder 23, the base plate 24, the pouch member 25, and the size adjusting sole 26 is a shape in which the sole shape portion 2 and the flare portion 3 are integrated and formed.

The edge of the nylon member 22 is sewn together with a thread and adhered to the edge of the pouch member 25, however it is not limited to this. The edge of the nylon member 22 may be, for example joined with the edge of the pouch member 25 by heat welding and the like.

On the toe side of the sensor holder 23, two first load sensors 4 and two sensor amplifiers 6 are provided respectively. On the heel side of the sensor holder 23, the first load sensor 4, the second load sensor 5 and the sensor amplifier 6 are provided respectively. A micro substrate 7 is provided with the approximate center portion of the sensor holder 23 (the plantar arch portion). A battery 8 projects outside and is provided with the approximate center portion of the sensor holder 23. The battery 8 provides an electrical power for the micro substrate 7 and the sensor amplifier 6.

For example, the micro substrate 7 may be formed by hardware mainly using a microcomputer including a CPU (Central Processing Unit) that performs arithmetic processing, a memory including a ROM (Read Only Memory) and/or a RAM (Random Access Memory) that stores an arithmetic program to be executed by the CPU, and an interface unit (I/F) that externally receives and outputs signals. The respective first and second load sensor 4, 5 is connected to the micro substrate 7 via the respective sensor amplifier 6. The respective first and second load sensor 4, 5 outputs the detected load value as a load signal to the respective sensor amplifier 6. The respective sensor amplifier 6 amplifies the load signal and outputs it to the micro substrate 7.

The CPU of the micro substrate 7 (a specific example of center calculation means) calculates the center of the load of the sole, for example based on the load signal outputted from the respective first and second load sensors 4, 5. The CPU of the micro substrate 7 outputs the calculated load center data to the driving unit 15. The controller of the driving unit 15 controls the motor according to the load center data from the micro substrate 7 to rotatably drive the knee joint portion 12 and assist the walking of a user.

The calibration data of the respective first and second load sensors 4, 5 is stored in the ROM or RAM (a specific example of storage means) of the micro substrate 7. The micro substrate 7, for example automatically outputs the stored calibration data to the driving unit 15 in the higher rank. Accordingly, it is unnecessary for a user to input the calibration data into the driving unit 15, thereby the convenience is high and it enables preventing the input mistake.

The micro substrate 7 outputs the afore-mentioned load center data and the calibration data via a wire to the driving unit 15, however it is not limited to this. The micro substrate 7 (a specific example of communication means) may have a wireless communication function such as a Bluetooth (a registered trademark) and the like. In this case, the micro substrate 7 outputs the afore-mentioned load center data and the calibration data via a wireless to the driving unit 15. Accordingly, when the load detecting device 1 is changed according to the size of the foot of the walk trainee (for example, in case two kinds of load detecting devices (size of 22 cm and 26 cm) are prepared) and the like, it is unnecessary to wire between the load detecting device 1 and the driving unit 15 and is convenient.

The base plate 24 is provided with the upper surface of the pouch member 25. A pair of load supporting pins 241 are provided at the position corresponding to the respective first load sensor 4 of the sensor holder 23 on the toe side of the base plate 24 (refer to FIG. 4). A pair of load supporting pins 241 are provided at the position corresponding to the respective first and second load sensor 4, 5 of the sensor holder 23 on the heel side of the base plate 24. The respective load supporting pin 241 projects in a upper direction and is provided with the upper surface of the base plate 24. The respective load supporting pin 241 abuts the corresponding respective impression portion of the first and second load sensors 4, 5 in the sensor holder 23.

The pouch member 25 is formed from e.g. an elastic resin and the like. The pouch member 25 is a case member which is open in the upper surface. The pouch member 25 stores the base plate 24 and the sensor holder 23 inside it. The opening of the upper surface of the pouch member 25 is covered with the nylon member 22. Accordingly, the first and second load sensors 4, 5, the sensor amplifier 6, and the micro substrate 7 of the sensor holder 23 are hermetically sealed and are protected from a dust, a water and the like.

The sensor holder 23 and the base plate 24 are located within the pouch member 25, and are unified with the size adjusting sole 26. Accordingly, the pouch member 25 securely locates the respective first and second load sensor 4, 5 of the sensor holder 23 and the respective load supporting pin 241 of the base plate 24.

Figure 4:
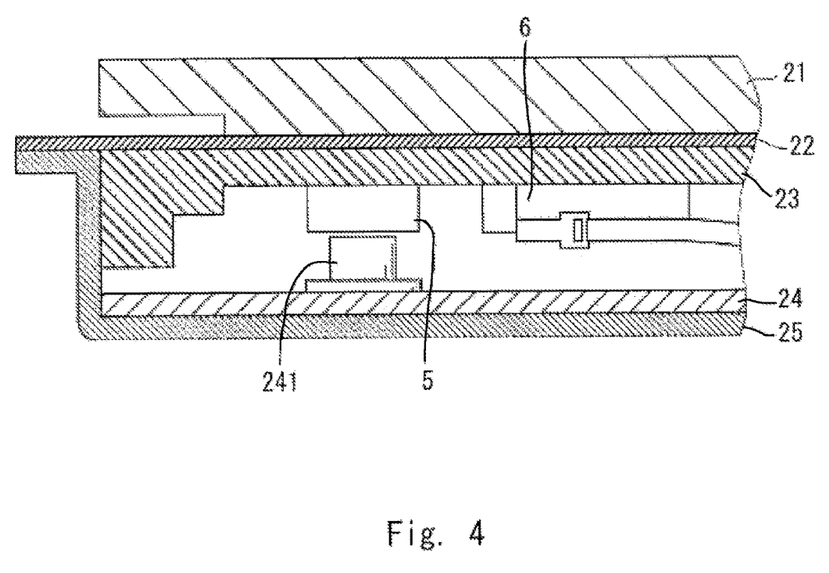
FIG. 4 is a partial cross section of a load detecting device according to an embodiment of the invention.

The distance of the space between the sensor holder 23 and the base plate 24 is for example approximately 2 mm. The impression portion of the first and second load sensors 4, 5 and the respective load supporting pin 241 are adjacent. Therefore, the escape to the other member at the time that the respective impression portion of the first and second load sensors 4, 5 pushes the respective load supporting pin 241, is reduced, thereby the load detecting accuracy can be improved.

The size adjusting sole 26 is provided on the pouch member 25 and covers it. The size adjusting sole 26 is prepared for example at 1 cm intervals from 26 to 29 cm.

As stated above, in the load detecting device 1 according to the embodiment, the second load sensor 5 detecting the load of the flare portion 3 is provided. Therefore, the detecting area of a sole of a walk trainee can be extended to the flare portion 3 to improve the detecting accuracy.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

Figure 5:
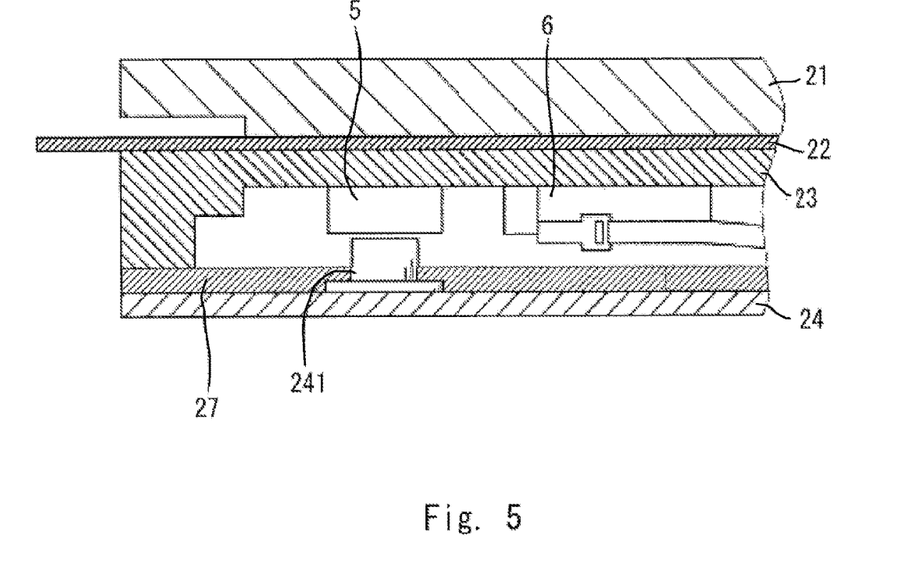
FIG. 5 is an illustration showing a constitution in which a low elastic resin is provided between a sensor holder and a base plate.

In the afore-mentioned embodiment, the low elastic resin 27 may be provided between the sensor holder 23 and the base plate 24 to locate the sensor holder 23 and the base plate 24 without the pouch member 25 (refer to FIG. 5). In this case, the low elastic resin 27 are required to be a soft material to reduce the load escaping to the low elastic resin 27. As the low elastic resin 27, e.g. a urethane rubber, a sponge and the like can be used.

Figure 6:
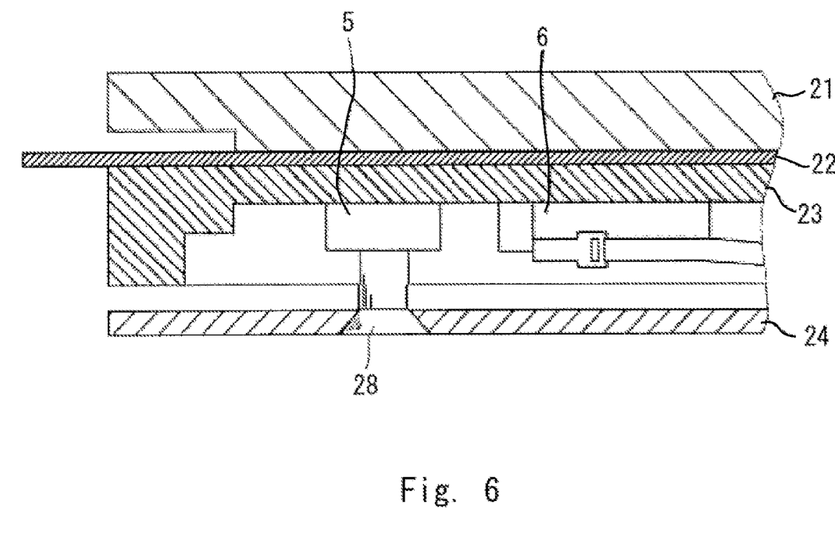
FIG. 6 is an illustration showing a constitution in which a base plate is directly provided with a respective first and second load sensor by using plate screws.

In the afore-mentioned embodiment, the base plate 24 may be directly mounted on the respective first and second load sensor 4, 5 by using a plate screw 28 and the like to locate the sensor holder 23 and the base plate 24 (refer to FIG. 6). In this case, the diameter of the first and second load sensors is increased, a tap for mounting is formed on the impression portion, and the plate screw 28 is screwed into the tap. Accordingly, the afore-mentioned load escape can be reduced.

In the afore-mentioned embodiment, the controller is provided within the driving unit 15, however it is not limited to this. The controller may be provided within e.g. a terminal device other than the driving unit 15. In this case, the walk assisting device 10 remotely is operated by the terminal device.

In the afore-mentioned embodiment, the micro substrate 7 is provided with the load detecting device 1, however it is not limited to this. The micro substrate 7 may be provided with the controller of the driving unit 15.

In the afore-mentioned embodiment, the load detecting device 1 is configured to be installed within the walk assisting device 10, however it is not limited to this. For example, the second load detecting device 1 may be independently equipped with a leg of a walk trainee. In addition, the second load detecting device 1 may be equipped with a good leg of a walk trainee, and the walk assisting device 10 including the first load detecting device 1 may be equipped with a affected leg. The controller of the driving unit 15 (a specific example of all center calculation means) can calculate the center of all load in grounding with both legs based on the load signal transmitted from the second load detecting device 1 of the good leg side and the first load detecting device 1 of the affected leg side via a wireless or a wire. The data of the center of all load becomes an effective data to make sure the movement of the center of gravity in the walk trainee. Accordingly, the efficiency of the training can be improved by using the effective data.

In the afore-mentioned embodiment, one flare portion 3 is provided on the heel side, however it is not limited to this. The flare portion 3 may be provided for example on the toe side or the plantar arch portion. A plurality of the flare portions 3 may be provided. In this case, the second load sensor 5 may be provided with the respective flare portion 3.

In the afore-mentioned embodiment, the load detecting device 1 may be constituted not to include the load supporting pin 241. For example, the first and second load sensors 4, 5 may be provided with the size adjusting sole 26, and the impression portion may be directly contact with a road surface and be pushed by it.

What is claimed is:

1. A load detecting device comprising:
   a sole shape portion configured to contour to an entire sole of a user;
   a flare portion projecting away from the sole shape portion;
   at least one first load sensor disposed within the sole shape portion and configured to detect a load on the sole shape portion;
   a second load sensor disposed within the flare portion and outside of the sole shape portion, the second load sensor being configured to detect a load on the flare portion separate from the load on the sole shape portion; and
   a load supporting pin projecting into the flare portion and extending towards the second load sensor such that the load supporting pin and the second load sensor are vertically aligned when the load detecting device is in use.

2. The load detecting device according to claim 1, further comprising a processor configured to calculate a center of a walking load on the sole of the user based on the loads detected by the first and second load sensors.

3. The load detecting device according to claim 1, further comprising three first load sensors, two of the three first load sensors are provided on a toe side of the sole shape portion, and one of the three first load sensors is provided on a heel side of the sole shape portion.

4. The load detecting device according to claim 1, further comprising a storage medium configured to store calibration data of the first and second load sensors.

5. The load detecting device according to claim 1, further comprising a transceiver configured to wirelessly transmit load data and/or calibration data of the first and second load sensors.

6. A walk assisting device comprising:
   the load detecting device according to claim 1;
   a thigh frame coupled to the load detecting device via an ankle joint portion;
   a crus frame coupled to the thigh frame via a knee joint portion; and
   a motor configured to drive the knee joint portion.

7. The walk assisting device according to claim 6, further comprising:
   a secondary load detecting device including:
      a secondary sole shape portion configured to contour to an entire second sole of the user;
      a secondary flare portion projecting away from the secondary sole shape portion;
      at least one secondary first load sensor disposed within the secondary sole shape portion and configured to detect a load on the secondary sole shape portion; and
      a secondary second load sensor disposed within the secondary flare portion and outside of the secondary sole shape portion, the secondary second load sensor being configured to detect a load on the secondary flare portion separate from the load on the secondary sole shape portion, and
   a main processor configured to calculate a center of a total walking load on the load detecting device and the secondary load detecting device, the center of the total walking load being based on the load detected by the first load sensor of the first load detecting device and the secondary second load sensor of the secondary load detecting device.

* * * * *